US007258428B2

(12) United States Patent
Reddy et al.

(10) Patent No.: US 7,258,428 B2
(45) Date of Patent: Aug. 21, 2007

(54) MULTIPLE HEAD CONCENTRIC ENCAPSULATION SYSTEM

(75) Inventors: Kiran Kumar Karrem Reddy, Roswell, GA (US); Sheldon John Hilger, Cumming, GA (US); Thomas Glenn Merrill, Cumming, GA (US); Joseph Mitchell, Alpharetta, GA (US); Richard I. Wolkowicz, Ellenton, FL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 150 days.

(21) Appl. No.: 10/954,312

(22) Filed: Sep. 30, 2004

(65) Prior Publication Data

US 2006/0066682 A1 Mar. 30, 2006

(51) Int. Cl.
*B41J 2/45* (2006.01)
*B41J 2/14* (2006.01)
*A61J 3/07* (2006.01)

(52) U.S. Cl. ............................... 347/68; 347/47; 264/4

(58) Field of Classification Search .................. 347/68
See application file for complete search history.

(56) References Cited

U.S. PATENT DOCUMENTS

| | | | | |
|---|---|---|---|---|
| 2,766,478 | A | 10/1956 | Ralley, Jr. et al. | 264/4 |
| 3,832,579 | A * | 8/1974 | Arndt | 310/326 |
| 3,922,360 | A | 11/1975 | Sneath | 426/573 |
| 4,119,739 | A | 10/1978 | Barwick et al. | 426/573 |
| 4,395,719 | A | 7/1983 | Majewski et al. | 347/68 |
| 4,672,397 | A * | 6/1987 | Suga et al. | 347/21 |
| 4,695,466 | A | 9/1987 | Morishita et al. | 424/456 |
| 4,806,357 | A | 2/1989 | Garrett et al. | 427/4 |
| 4,828,780 | A | 5/1989 | Luker | 264/171.21 |
| 5,399,368 | A * | 3/1995 | Garwood et al. | 426/307 |
| 6,328,409 | B1 | 12/2001 | Peeters et al. | 347/21 |
| 6,377,387 | B1 * | 4/2002 | Duthaler et al. | 359/296 |
| 6,406,747 | B1 | 6/2002 | Biegelsen et al. | 427/213.34 |
| 6,416,172 | B2 | 7/2002 | Jeong et al. | 347/72 |
| 6,445,490 | B1 | 9/2002 | Chopra et al. | 359/296 |

(Continued)

FOREIGN PATENT DOCUMENTS

GB 1564452 4/1980

(Continued)

OTHER PUBLICATIONS

Patent Abstracts of Japan, Publication No. 61011139 A, Jan. 18, 1986.

*Primary Examiner*—Matthew Luu
*Assistant Examiner*—Shelby Fidler
(74) *Attorney, Agent, or Firm*—Sue C. Watson

(57) ABSTRACT

A multi-headed ink-jet system adapted to eject encapsulated liquids is provided, which includes a plurality of concentric piezoelectric members. Each concentric piezoelectric member has a chamber configured to carry a liquid therethrough, and each concentric piezoelectric member is in liquid communication with an exit port provided in a concentric orifice. When each concentric piezoelectric member is actuated, a liquid contained in its chamber is moved near or through the concentric orifice. The plurality of concentric piezoelectric members cooperate to control the ejection of liquids through the concentric orifice to permit one liquid to be encapsulated by another liquid to form an encapsulated droplet. A method of operating a multi-headed ink-jet system adapted to eject encapsulated liquids.

28 Claims, 4 Drawing Sheets

U.S. PATENT DOCUMENTS

| | | | | |
|---|---|---|---|---|
| 6,599,627 | B2 * | 7/2003 | Yeo et al. | 428/402.21 |
| 6,793,949 | B2 * | 9/2004 | Panesar | 426/93 |
| 2003/0013783 | A1 * | 1/2003 | Kommareddi et al. | 523/175 |
| 2003/0091696 | A1 | 5/2003 | Panesar | 426/93 |

FOREIGN PATENT DOCUMENTS

| | | |
|---|---|---|
| GB | 2192171 | 1/1988 |

* cited by examiner

MULTIPLE HEAD CONCENTRIC ENCAPSULATION SYSTEM

BACKGROUND

This invention relates to the field of ink jet printers, and more particularly, to the field of mechanisms utilized to project ink or other liquids from orifices.

It is often desirably to add ingredients to a woven or non-woven web or substrate to enhance the qualities of the web and offer additional features. One example of an added ingredient is an aloe-based emollient added to a cellulose-based web, to add both softness and other features contained in the aloe.

A problem exists, however, in applying multi-component mixtures, such as, but not by way of limitation, microemulsions, to a web. Such mixtures tends to destabilize upon contact with the web. Further, due to this destabilization, the efficacy of the active ingredient(s) tends to decrease. Migration of the mixture or some ingredients of the mixture within the web matrix is also of great concern. In addition, such multi-component mixtures tend to destabilize upon contact with a web or substrate. In order to better control the application and maintenance of a multi-component mixture on a web, it is necessary to deposit the ingredients at specific sites and protect their composition once it is deposited on a substrate or a web.

To address these problems, a multi-headed concentric ink-jet print system is utilized. Such a system desirably has a chamber provided by piezoelectric heads or members having piezo-electric crystals. The piezoelectric heads or members are connected to a control system, which permit the inner chamber to eject a droplet of a multi-component mixture or encapsulant while, simultaneously, an outer chamber surrounding the inner chamber ejects an encapsulating agent. As the mixture generally forms a spherical droplet, the encapsulating agent simultaneously provides an outer coating such that when the droplet is completely formed and ejected, the encapsulant is completely encapsulated.

Such a system permits encapsulation of a single liquid or a mixture of liquids. Similarly, such a system also permits greater control of the size and shape of the droplets, as well as the arrangement, positioning and distribution of the encapsulated droplets on a substrate or web. Such a system may utilize both piezo-electric heads or members and pneumatic pressure to control the ejection of encapsulated droplets.

DEFINITIONS

As used herein the following terms have the specified meanings, unless the context demands a different meaning, or a different meaning is expressed; also, the singular generally includes the plural, and the plural generally includes the singular unless otherwise indicated.

As used herein, the terms “comprises”, “comprising” and other derivatives from the root term “comprise” are intended to be open-ended terms that specify the presence of any stated features, elements, integers, steps, or components, but do not preclude the presence or addition of one or more other features, elements, integers, steps, components, or groups thereof.

As used herein, the term “nonwoven” means either a nonwoven web, a film, a foam sheet material, or a combination thereof.

As used herein the term “nonwoven web” means a web having a structure of individual fibers, filaments or threads which are interlaid, but not in an identifiable manner as in a knitted fabric. Fibrous nonwoven fabrics or webs have been formed from many processes such as for example, meltblowing processes, spunbonding processes, and bonded carded web processes. The basis weight of fibrous nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term “liquid” refers to the state of matter in which a substance exhibits a characteristic readiness to flow, little or no tendency to disperse, and relatively high incompressibility.

As used herein, the term “cellulose”, or “cellulosic material” refers to material that may be prepared from cellulose fibers from synthetic sources or natural sources, such as woody and non-woody plants. Woody plants include, for example, deciduous and coniferous trees. Non-woody plants include, for example, cotton, flax, esparto grass, milkweed, straw, jute, hemp, and begasse. The cellulose fibers may be modified by various treatments such as, for example, thermal, chemical, and/or mechanical treatments. It is contemplated that reconstituted and/or synthetic cellulose fibers maybe used and/or blended with other cellulose fibers of the fibrous cellulosic material.

As used herein, the term “encapsulant” refers to material, including, but not limited to, liquid, used for encapsulating.

As used herein, the term “encapsulating” or “encapsulating agent” refers to encasing an item in or as if in a capsule.

These terms may be defined with additional language in the remaining portions of the specification.

SUMMARY OF THE INVENTION

In response to the difficulties and problems discussed above, a multi-headed ink-jet system adapted to eject encapsulated liquids is provided. The system includes a plurality of concentric piezoelectric members. Each concentric piezoelectric member has a chamber configured to carry a liquid therethrough, and each concentric piezoelectric member is in liquid communication with an exit port provided in a concentric orifice. When each concentric piezoelectric member is actuated, it moves a liquid contained in its chamber near or through the concentric orifice. The plurality of concentric piezoelectric members cooperate to control the ejection of liquids through the concentric orifice to permit one liquid to be encapsulated by another liquid to form an encapsulated droplet.

DETAILED DESCRIPTION

Figure 1:
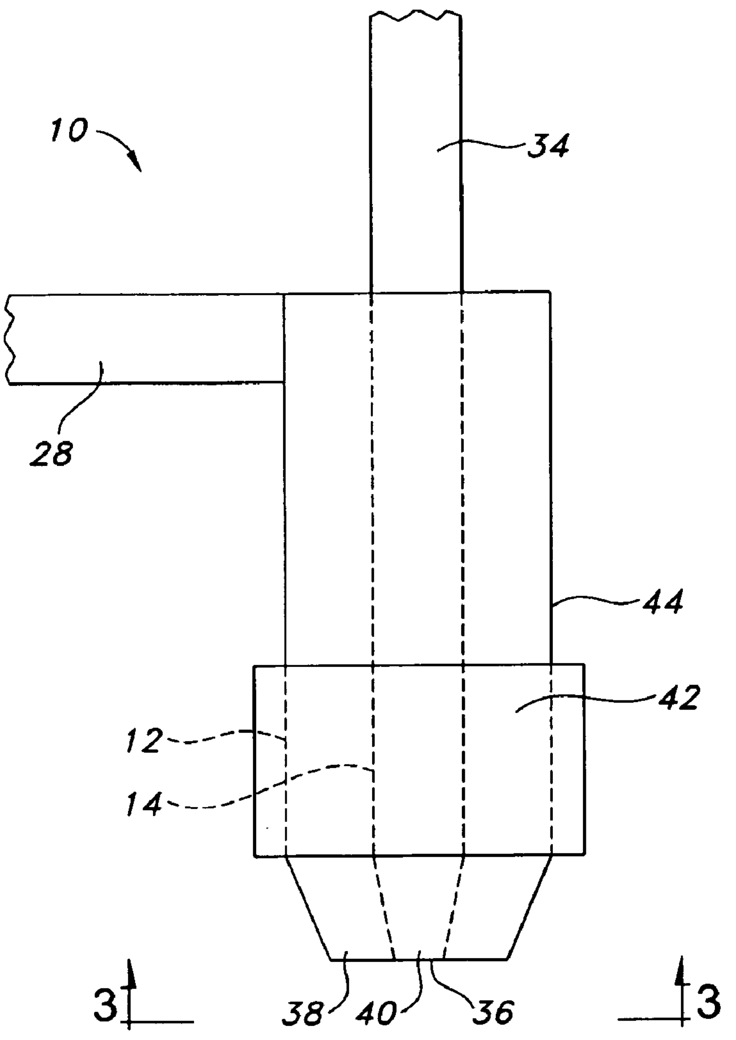
FIG. 1 is a side view of the multi-headed ink-jet system of the present invention, showing the multi-headed ink jet.

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The present invention provides a concentric multiple headed ink jet printing system which includes multiple reservoirs in liquid communication with concentric conduits, that is, concentric tubular piezoelectric members, which terminate in a concentric orifice and deliver therethrough an encapsulant and an encapsulating agent. The piezoelectric members desirably include an outer piezoelectric member having a chamber which surrounds and is axially aligned with an inner piezoelelctric member having a chamber therein. The encapsulant and the encapsulating agent are desirably ejected from the concentric orifice such that the encapsulating agent fully encapsules the encapsulant just before being completely ejected or separated from the concentric orifice. Each of the concentric piezoelectric members desirably, but not by way of limitation, comprises a substantially flexible elastomeric tubular member characterized by electromechanical transducer properties which may be achieved by dispersing piezoelectric crystals in each tubular member. Each flexible piezoelectric member desirably has one or more electrodes defined along its outer surface for selectively creating transient peristaltic-like constrictions in the piezoelectric member to generate and reinforce desired pressure waves which advance toward the concentric orifice, so that liquids or substances contained in a chamber of each piezoelectric member advances toward and through the concentric orifice. In addition thereto, pneumatic pressure is utilized to further control the ejection of droplets from the concentric orifice.

A multi-headed liquid jet system provided by a dual headed ink-jet print system is used to apply various substances, such as, but not by way of limitation, chemicals, aqueous liquids, oil-based liquids, lotions, and so forth, to a web. Such webs desirably, include but are not limited to non-woven cellulose-based webs, woven cellulose-based webs, webs containing both non-woven cellulose and non-woven synthetic fibers, webs containing non-woven synthetic fibers, polymer foams, both extruded and/or film casted, a combination of two or more of the above mentioned substrates, and so forth. In this manner, a substance may be extruded in droplet form and simultaneous surrounded and encapsulated during the extrusion process by an encapsulating agent which is extruded over the encapsulated substance.

The multi-headed system will allow targeting the active ingredients with site specificity and event driven specificity. For example, a silicone or ceramic based material may be used as an encapsulating agent to provide an outer shell and a soap/degreasing agent may be used to provide an inner core or encapsulant. The encapsulated soap/degreasing agent would desirably be deposited by the system on a wiper, with the potential that both the outer shell (encapsulating agent) and the inner core (encapsulant) would be used as a grit/soap when the wiper was used. That is, the efficacy of the soap/degreasing agent is preserved until the user presses on the wiper (pressure triggered, event driven), thereby crushing the hard outer shell while releasing the soap/degreasing agent. The crushed shell then acts as an abrasive and aids in the function of the active ingredient (soap/degreasing agent) in the effective removal of grease, and so forth. Further, different combinations could be used on different surfaces of a wiper, such as, for example, an encapsulated degreasing agent on one surface of a wiper and an encapsulated anti-bacterial agent on an opposite surface of the wiper.

Figure 3:
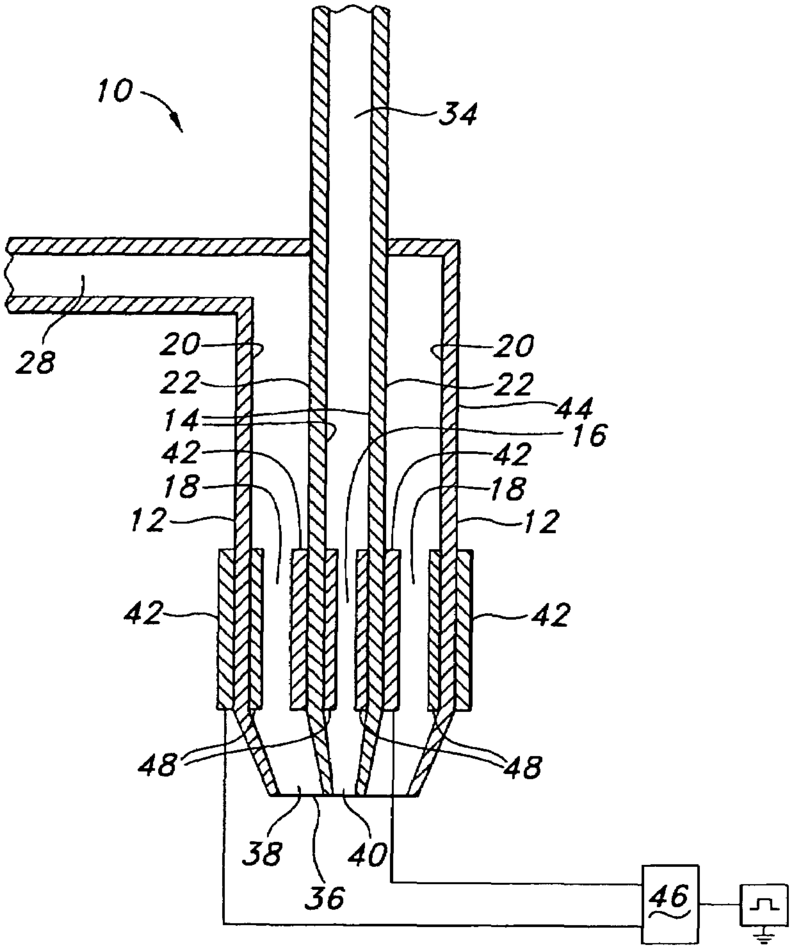
FIG. 3 is a schematic view of FIG. 1 taken along line 3, showing the outer and inner piezoelectric members and their chambers.

Referring to FIGS. 1 and 3, a multi-headed ink-jet system 10 is illustrated which comprises an outer piezoelectric member 12 and an inner piezoelectric member 14. The outer piezoelectric member 12 is positioned over the inner piezoelectric member 14 in a desirably concentric orientation such that, when viewed in a horizontal cross section (not shown), the outer and inner piezoelectric members 12, 14 appear as circles of a different size having a common center, one within another. While this concentric orientation is desirable, it is not intended as a limitation; an eccentric orientation may also be used. Moreover, while a circular cross-section is described, the cross-section may include any geometric or asymmetric configuration(s).

Figure 4:
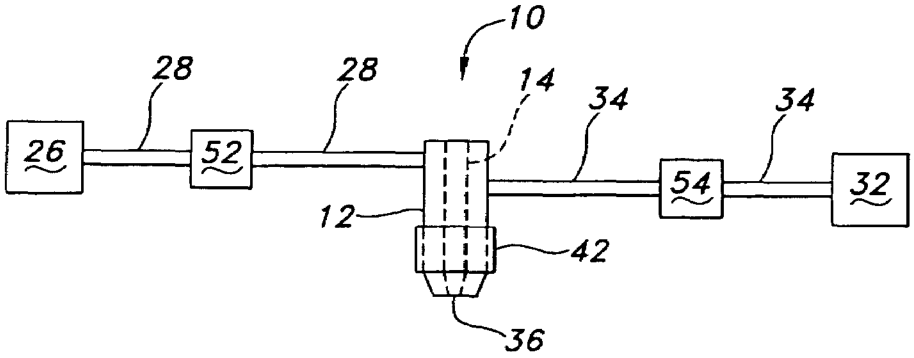
FIG. 4 is a diagrammatic illustration of the multi-headed ink-jet system showing conduits, pumps and reservoirs.

The inner piezoelectric member 14 is defined by an inner chamber 16 which is formed therein. The outer piezoelectric member 12 also includes an outer chamber 18 which is formed between an inner surface 20 of the outer piezoelectric member 12 and an outer surface 22 of the inner piezoelectric member 14. The system 10 is includes a first liquid 24 (FIGS. 5A-5D) which is carried from a first liquid supply or reservoir 26 via a first conduit 28 to the outer chamber 18 of the outer piezoelectric member 12, as shown in FIG. 4. Similarly, a second liquid 30 is carried from a second liquid supply or reservoir 32 via a second conduit 34 to the inner chamber 16 of the inner piezoelectric member 14.

Figure 2:
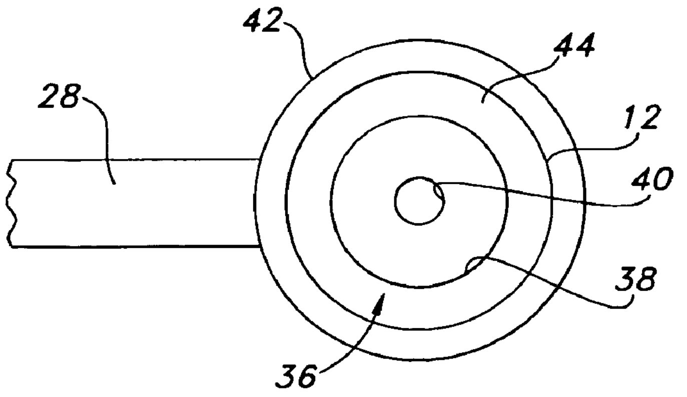
FIG. 2 is a plan view of the lower end of the multi-headed ink-jet system of FIG. 1, showing the concentric orifice and the first and second exit ports.

The outer and inner piezoelectric members 12, 14 terminate at a concentric orifice 36, as illustrated by FIGS. 2 and 3. The concentric orifice 36 includes a first exit port 38 from the outer chamber 18 of the outer piezoelectric member 12 through which the first liquid 24 is ejected or extruded. The concentric orifice 36 also includes a second exit port 40 from the inner chamber 16 of the inner piezoelectric member 14 through which the second liquid 30 is ejected or extruded. The concentric orifice 36 and the first and second exit ports 38, 40 are desirably smaller than an internal diameter of the outer and inner chambers 18, 16 of the outer and inner piezoelectric members 12, 14. Both the first and second liquids 24, 30 in the present embodiment are desirably, but not by way of limitation, ejected in droplet form, which will be described in further detail below.

Turning to FIG. 3, the outer and inner piezoelectric members 12,14 each carry a conductive coating 42 on each outer surface 44, 22, respectively, which is energized by a suitable power source via pulses controlled by a controller 46. The outer and inner chamber 18, 16 of each outer and inner piezoelectric member 12, 14 is in liquid communication with the first and second liquid reservoirs 26, 32 via the first and second conduits 28, 34 and with the first and second exit ports 38, 40 of the concentric orifice 36, as shown diagrammatically in FIG. 4.

The outer and inner piezoelectric members 12, 14 are constructed to have elasticity and sufficient electromechanical transducer properties to permit the volume of the outer and inner chambers 18, 16 to contract and to expand to the point that contraction of each inner and outer chamber 18, 16 via actuation of each outer and inner piezoelectric member 12, 14 results desirably in the ejection or extrusion of a droplet through the concentric orifice 36 in response to pulses from the power source via the controller 46.

In the present embodiment, the characteristics of the outer and inner piezoelectric members 12, 14 are desirably, but not by way of limitation, provided by a substantially uniformly dispersed or homogeneous mixture of piezoelectric crystals and an elastic binder. For example, the piezoelectric crystals may include PZT powder and the elastic binder may include neoprene rubber. In the present embodiment, NTK™ piezorubber materials, available from NTK Technology, 3255-2 Scott Boulevard, Santa Clara, Calif. 95054, may be utilized. In addition, 5 to 15 parts of a plasticizer such as styrene or asphalt may be added with 1 to 3 parts of sulfur. This mixture may then be formed into the outer and inner piezoelectric members 12, 14 vulcanized and subjected to an electric field so as to properly polarize the piezoelectric crystals. The conductive coating 42 may then be applied to each outer and inner piezoelectric member 12, 14 to permit actuation thereof. In addition, the interior of each outer and inner piezoelectric member 12, 14 may include an interior conductive coating 48 as well (FIG. 3). Similar or other operative materials and/or mechanisms which may also be appropriate for use with the present invention are available through NTK Technology.

Such piezoelectric members are described in detail in U.S. Pat. No. 4,395,719 issued Jul. 26, 1983, to Majewski et al., which is hereby incorporated by reference in its entirety for all purposes herein. Alternatively, piezoelectric actuators may be formed in or into tubes or other appropriate conduits (not shown). Piezoelectric deformation of such piezoelectric bodies occurs when a voltage from a power source is applied to the piezoelectric bodies via a common electrode or conductive coating positioned on one end of the piezoelectric body and a driving electrode or conductive coating positioned on an opposite end of each piezoelectric body. The deformation of the piezoelectric body causes a change in the volume in each chamber of each actuated piezoelectric body, causing a discharge of liquid droplets through a nozzle. Such piezoelectric bodies are shown and described in detail in U.S. Pat. No. 6,416,172, issued Jul. 9, 2002 to Jeong, et al., which is hereby incorporated by reference in its entirety for all purposes herein. It will be appreciated that other piezoelectric mechanisms known in the art may be used in the present invention.

Referring now to FIGS. 1-3, the outer piezoelectric member 12 is illustrated coated with an axially displaced ring-like conductive coating 42. Similarly, the inner piezoelectric member 14 is shown with an axially displaced ring-like conductive coating 42. Each conductive coating 42 may be selectively energized such that: (a) each coating is energized sequentially, or (b) each coating is energized simultaneously with the other, or (3) each coating is energized independently of the other which may be sequential and/or simultaneous. Each conductive coating 42 is energized via the power source by means of the control circuit or controller 46, and so forth. This allows a pressure wave to be produced within each chamber of each actuated piezoelectric member, which moves a liquid held in the chamber toward and/or through the concentric orifice. It will be appreciated that the liquid in the chamber is in liquid communication with the liquid in the conduit and reservoir.

Figure 5A:
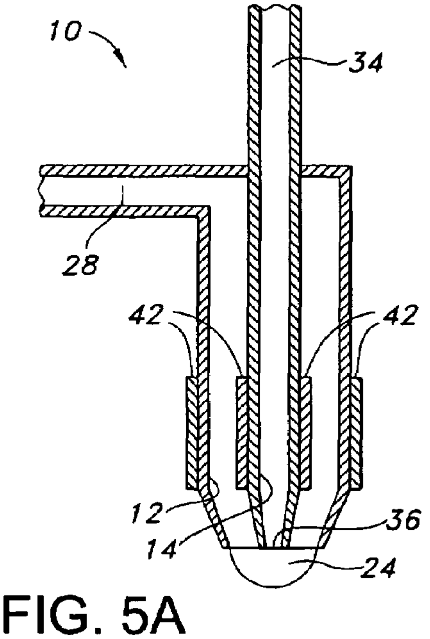
FIG. 5A is a schematic view similar to FIG. 3, but showing a first liquid being partially ejected from the concentric orifice.
Figure 5B:
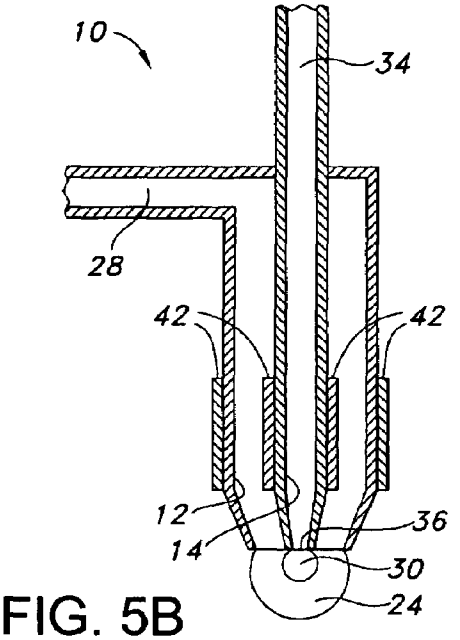
FIG. 5B is a schematic view similar to FIG. 5A, but showing a second liquid being introduced into the center of the first liquid.
Figure 5C:
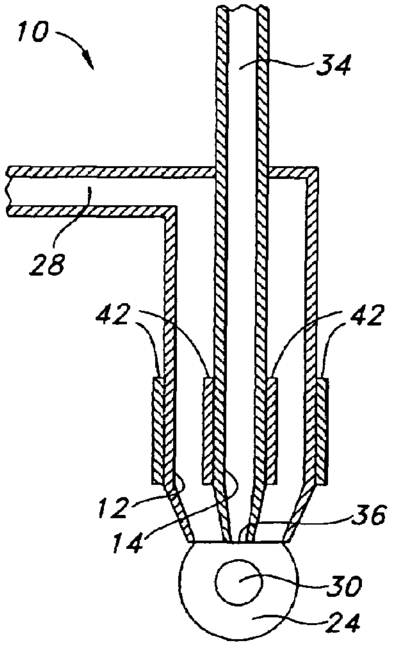
FIG. 5C is a schematic view similar to FIG. 5B, but showing the second liquid being completely surrounded by the first liquid while a portion of the first liquid is still positioned against the concentric orifice.
Figure 5D:
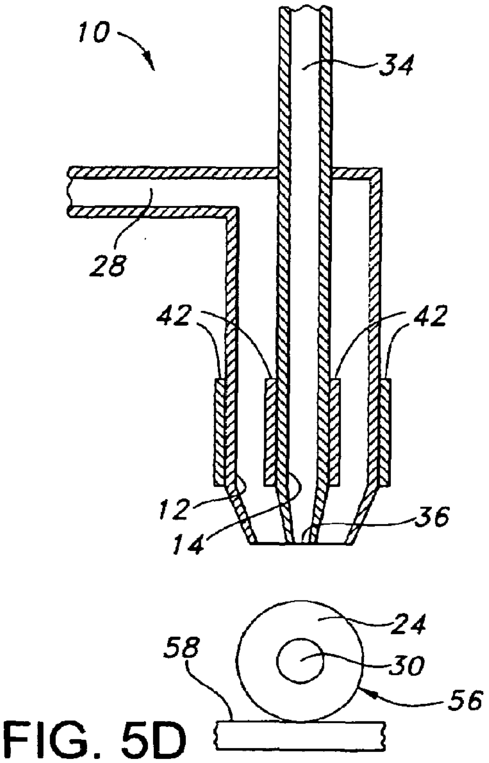
FIG. 5D is a schematic view similar to FIG. 5C, but showing the first liquid encapsulating the second liquid as an encapsulated droplet which is ejected from the concentric orifice and disposed on a web.
Figure 6:
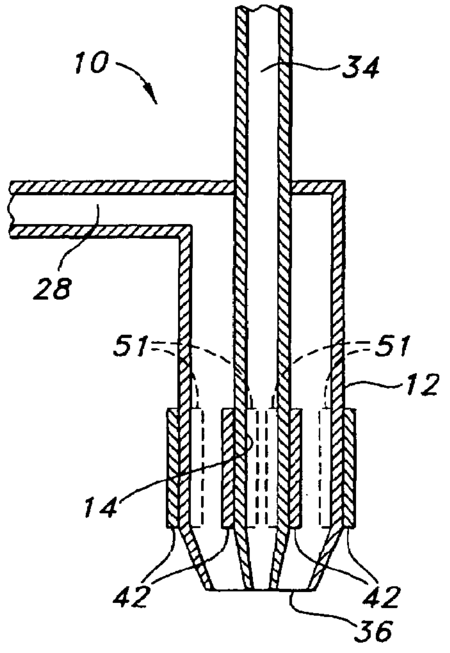
FIG. 6 is a schematic view similar to FIG. 3, but showing the deformation of the outer and inner chambers of the outer and inner piezoelectric members, respectively, via the phantom lines.

As noted previously, energizing the conductive coating 42 of the outer and inner piezoelectric members 12, 14 results in their actuation, causing deformation of the outer and inner chambers 18, 16, as illustrated in FIG. 6 (by the phantom lines designated generally by the numeral 51), thereby pushing the liquid contained therein toward the concentric orifice 36 for ejection as an encapsulated droplet, as illustrated in FIGS. 5A-5D. Such actuation may be enhanced and further controlled by controlling the pressure of the liquid within the outer and inner chambers 18, 16 and near or at the concentric orifice 36 by first and/or second pneumatic pumps 52, 54.

Depending upon the liquid(s) contained in the reservoir (s), a first pneumatic pump 52 and/or a second pneumatic pump 54 may be used to more accurately control the ejection or extrusion of droplets through the concentric orifice 36. By way of non-limiting example, as illustrated in FIG. 4, the first pneumatic pump 52 and the second pneumatic pump 54 are placed in liquid communication with each first and second conduit 28, 34, respectively, to assist in more finely controlling the liquid ejected from each first and second exit port 38, 40 in the concentric orifice 36. In this manner, during the process of ejection, the second liquid 30 is at least surrounded, and desirably encapsulated, by the first liquid 24 as an encapsulated droplet 56 prior to complete separation of the droplet from the concentric orifice 36, as shown in FIGS. 5A-5D.

Turning now to the ejection of a first liquid 24 and a second liquid 30 to form the encapsulated droplet 56, FIG. 5A shows a first liquid 24 beginning to emerge from the concentric orifice 36. FIG. 5B illustrates the second liquid 30 emerging via the concentric orifice 36 into, desirably, an interior of a partial sphere or droplet being formed by the first liquid 24. FIG. 5C shows the second liquid 30 forming, desirably, a spherical inner core within the first liquid 24 as the first liquid 24 surrounds the spherical inner core of the second liquid 30, the first liquid 24 providing an outer coating or complete capsule around the inner core provided by the second liquid 30, while the first liquid 24 is still positioned against the concentric orifice 36. FIG. 5D illustrates the completely encapsulated droplet 56 as it is ejected or extruded away from the concentric orifice 36 by the piezoelectric deformation of at least one of the inner and outer chambers 16, 18 of the outer and inner piezoelectric members 12, 14. The droplet 56 is desirably disposed on a web 58.

It will be understood that pneumatic pressure via the first and/or second pumps 52, 54 may be utilized as well. In this instance, pneumatic pressure via the first and/or second pumps 52, 54 (FIG. 4) assists in movement and/or control of the first and second liquid 24, 30 as it moves from the first and second reservoirs 26, 32 through the first and second conduits 28, 34 and the outer and inner chambers 18, 16 of the outer and inner piezoelectric members 12, 14 is and ejected from the concentric orifice 36 as encapsulated droplets 56 (not shown).

Figure 7:
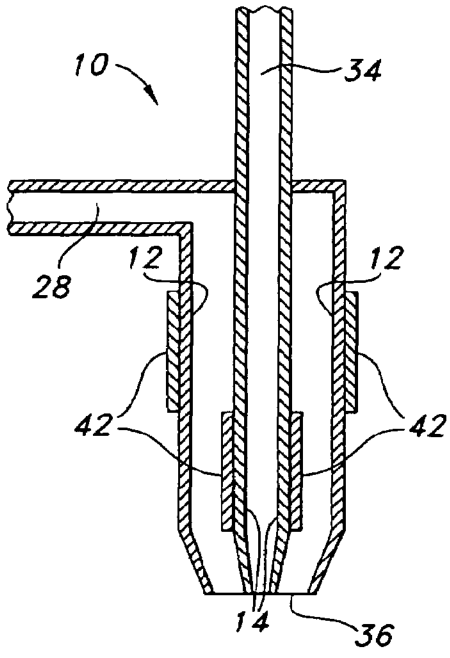
FIG. 7 is a schematic view similar to FIG. 3, but showing the outer piezoelectric member positioned axially higher relative to the inner piezoelectric member.
Figure 8:
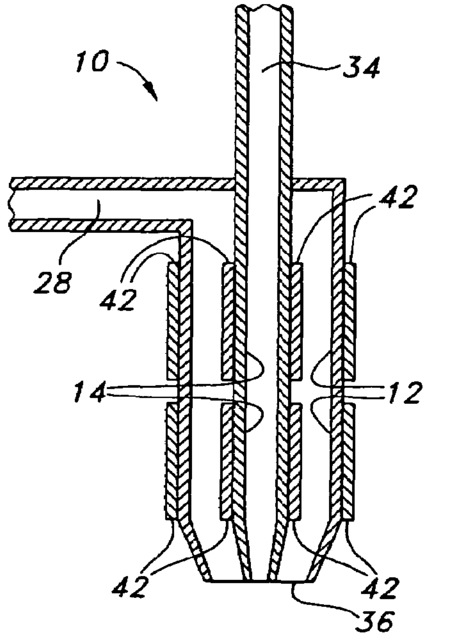
FIG. 8 is a schematic view similar to FIG. 3, but showing a pair or outer piezoelectric members and a pair of inner piezoelectric members.

As illustrated in FIG. 7, the each conductive coating 42 of the outer and inner piezoelectric members 12, 14 are not necessarily in axial alignment. In addition, as shown in FIG. 8, a plurality of conductive coatings 42 maybe be applied to each of the outer and inner piezoelectric members 12, 14 and actuated by the power source via the controller 46. Further, while an outer and inner piezoelectric member 12, 14 is illustrated, it will be understood that any number of concentric piezoelectric members may be utilized.

The encapsulated droplets 56 are desirably disposed on the web 58 or suitable substrate. The system 10 using piezoelectric members, or a combination of piezoelectric members 12, 14 and one or more pneumatic pumps, permit the system to control the dispersal of the droplets on the web, so that the droplets may be formed of a uniform size, and distributed on or in a web in a localized manner, a non-localized, evenly distributed manner, or any combination thereof.

A number of different liquids or mixtures may be encapsulated. Such encapsulants may include, but are not limited to, aqueous and/or oil based formulations, such as formulations for cleaning, deodorizing, disinfecting, and/or sanitizing surfaces and/or hard floors or emulsion formulations for cleaning, hydrating, moisturizing, deodorizing, disinfecting and/or sanitizing human or animal skin surfaces. Further, these encapsulants may include enzymes or formulations consisting in part of enzymes, to accomplish any, some of, or all of the tasks mentioned above. These encapsulants may also include, oxygen sensitive, light sensitive, pH sensitive and/or temperature sensitive polymer(s) which are responsive to environmental changes.

Similarly, a number of different encapsulating agents may be used. Such encapsulating agents may include, but are not limited to, the following: (1.) aqueous systems, such as, for example, gelatin, sodium alginate, gum arabic, functional cellulose derivatives, carrageenan, starches, functionally modified starches and their mixtures, (2.) hot melt systems which include waxes, fats, fatty acids, salts of fatty acids, poly ethylene glycol, glycerin and their mixtures, (3.) silicon containing polymers or oligomers with reactive functional groups, such as, for example, amino, acrylate, methacrylate or vinyl groups, (4.) polymers or oligomers sysnthesized or made reactive by an enzymatic action, (5.) photo crosslinkable polymers such as, for example, polyesters of p-phenylenedi-acrylic acid, diphenylcyclopropene derivates of poly (vinyl alcohol), poly (vinyl cinnamate), and so forth, and (6.) chitin and chitosan derivatives. The physical properties of the encapsulating agent are desirably chosen such that upon exiting or being ejected from the print head, the higher temperature, pressure, and exposure to standard room temperatures and pressures causes the encapsulating agent to harden into an outer shell, thereby protecting the inner encapsulant.

Ideally, the droplets may be controlled to have a variety of sizes. Such sizes are desirably controlled so that droplets of uniform size are distributed on a web. The desirable size of such droplets, for example, but not way of limitation are, in a range of about 50 nm to about 3 mm.

The dispersion of the droplets are controlled by a combination of flow rates of the encapsulants, encapsulating agents, the vibrational frequency of the individual piezoelectric members, the degree of synchronization between the individual piezoelectric members, an auxiliary pneumatic stream to divert and/or distribute the formed shells or ultrasonically oscillate and/or vibrate the entire coaxial assembly.

It will be appreciated that the driving force for ejecting the encapsulant surrounded by the encapsulating agent as a droplet may be both pneumatic and piezoelectric. Further, the size distribution of the droplets is a function of the pneumatic pressure, orifice diameter, viscosity of the liquids providing both the encapsulant and the encapsulating agent, and "control volume", dictated partially by the coaxial piezoelectric members and their chambers. Further, the "control volume" is be defined as the volume bounded by the size of the piezoelectric members and the temporary imaginary boundaries created by the vibrating piezoelectric members and would be equal to the corresponding volume of liquid expelled or ejected from the respective chambers with each oscillation.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A multi-headed ink-jet system adapted to eject encapsulated liquids, comprising:

at least two concentric piezoelectric members, each concentric piezoelectric member having an inner conductive coating and an outer conductive coating and each concentric piezoelectric member having a chamber formed therein configured to carry a liquid therethrough, an inner concentric piezoelectric member comprising an inner conductive coating positioned on an inner surface of an inner chamber and an outer conductive coating positioned against an outer surface of the inner chamber, the outer surface of the inner chamber providing at least a portion of an outer chamber, an outer concentric piezoelectric member comprising an inner conductive coating positioned on an inner surface of the outer chamber and an outer conductive coating positioned against an outer surface of the outer chamber, the chambers of each concentric piezoelectric member in liquid communication with an exit port provided in a concentric orifice, wherein actuation of the inner conductive coating of the inner concentric piezoelectric member affects liquid movement in both the inner chamber of the inner concentric piezoelectric member and the outer chamber of the outer concentric piezoelectric member, wherein actuation of the outer conductive coating of the inner concentric piezoelectric member affects liquid movement in both the inner chamber of the inner concentric piezoelectric member and the outer chamber of the outer concentric piezoelectric member, wherein actuation of the inner conductive costing and the outer conductive coating of the outer concentric piezoelectric member affects liquid movement only in the outer chamber of the outer concentric piezoelectric member, and wherein each of the inner and outer conductive coatings of each of the inner and outer concentric piezoelectric members are individually controlled to permit the ejection of liquids through the inner and outer chambers and through the concentric orifice to allow one liquid to be encapsulated by another liquid to form an encapsulated droplet prior to being detached from the concentric orifice.

2. The multi-headed ink-jet system of claim 1, wherein the outer chamber surrounds and is axially aligned with the inner chamber.

3. The multi-headed ink-jet system of claim 2, wherein the outer concentric piezoelectric member connects to a first conduit which is in liquid communication with a first reservoir.

4. The multi-headed ink-jet system of claim 3, wherein a pneumatic pump is in liquid communication with the first conduit, and wherein the pneumatic pump assists in controlling the ejection of liquids through the concentric orifice.

5. The multi-headed ink-jet system of claim 2, wherein the inner piezoelectric concentric member connects to a second conduit which is in liquid communication with a second reservoir.

6. The multi-headed ink-jet system of claim 5, wherein a pneumatic pump is in liquid communication with a second conduit, and wherein the pneumatic pump assists in controlling the ejection of liquids through the concentric orifice.

7. The multi-headed ink-jet system of claim 2, wherein the outer chamber of the outer concentric piezoelectric member is in liquid communication with a first exit port in the concentric orifice.

8. The multi-headed ink-jet system of claim 7, wherein a first liquid flows from a first reservoir through a first conduit to the outer chamber of the outer concentric piezoelectric member to be ejected through the concentric orifice, and wherein the first liquid includes an encapsulating agent.

9. The multi-headed ink-jet system of claim 2, wherein the inner chamber of the outer concentric piezoelectric member is in fluid communication with a second exit port in the concentric orifice.

10. The multi-headed ink-jet system of claim 9, wherein a second liquid flows from a second reservoir through a second conduit to the inner chamber of the inner piezoelectric member to be ejected through the concentric orifice, and wherein the second liquid includes an encapsulant.

11. The multi-headed ink-jet system of claim 2, wherein the concentric orifice includes a first exit port in liquid communication with the outer chamber and a second exit port in liquid communication with the inner chamber.

12. The multi-headed ink-jet system of claim 1, wherein each of the inner and outer conductive coatings of each of the inner and outer concentric piezoelectric members is individually actuated by a power source controlled by a controller.

13. The multi-headed ink-jet system of claim 12, wherein actuation of each of the inner and outer conductive coatings of the inner concentric piezoelectric member results in deformation of both the inner chamber of the inner concentric piezoelectric member and the deformation of the outer chamber of the outer concentric piezoelectric member.

14. The multi-headed ink-jet system of claim 12, wherein actuation of each of the inner and outer conductive coatings of the outer concentric piezoelectric member results in deformation of only the outer chamber of the outer concentric piezoelectric member without affection the inner chamber at the inner concentric piezoelectric member.

15. A multi-headed ink-jet system adapted to eject encapsulated liquids, comprising:

at least two concentric piezoelectric members, each concentric piezoelectric member having an inner conductive coating and an outer conductive coating and each concentric piezoelectric member having a chamber formed therein configured to carry a liquid therethrough, an inner concentric piezoelectric member comprising an inner conductive coating positioned on an inner surface of an inner chamber and an outer conductive coating positioned against an outer surface of the inner chamber, the outer surface of the inner chamber providing at least a portion of an outer chamber, an outer concentric piezoelectric member comprising an inner conductive coating positioned on an inner surface of the outer chamber and an outer conductive coating positioned against an outer surface of the outer chamber, the chambers of each concentric piezoelectric member in liquid communication with an exit sort provided in a concentric orifice, wherein actuation of the inner conductive coating of the inner concentric piezoelectric member affects liquid movement in both the inner chamber of the inner concentric piezoelectric member and the outer chamber of the outer concentric piezoelectric member, wherein actuation of the outer conductive coating of the inner concentric piezoelectric member affects liquid movement in both the inner chamber of the inner concentric piezoelectric member and the outer chamber of the outer concentric piezoelectric member, wherein actuation of the inner conductive coating and the outer conductive coating of the outer concentric piezoelectric member affects liquid movement only in the outer chamber of the outer concentric piezoelectric member, and wherein each of the inner and outer conductive coatings of each of the inner and outer concentric piezoelectric members are individually controlled, and a pneumatic pump in liquid communication with at least one liquid, wherein each of the inner and outer concentric piezoelectric members and the pneumatic pump are individually controlled and they together cooperate to permit the ejection of liquids through the concentric orifice to allow at least one liquid to be encapsulated by at least another liquid to form an encapsulated droplet.

16. The multi-headed ink-jet system of claim 15, wherein the outer chamber surrounds and is axially aligned with the inner chamber.

17. The multi-headed ink-jet system of claim 16, wherein the outer concentric piezoelectric member connects to first conduit which is in liquid communication with a first reservoir.

18. The multi-headed ink-jet system of claim 17, wherein the pneumatic pump is in liquid communication with the first conduit.

19. The multi-headed ink-jet system of claim 16, wherein inner concentric piezoelectric member connects to second conduit which is in liquid communication with a second reservoir.

20. The multi-headed ink-jet system of claim 19, wherein the pneumatic pump is in liquid communication with second conduit.

21. The multi-headed ink-jet system of claim 16, wherein the outer chamber of the outer concentric piezoelectric member is in liquid communication with a first exit port in the concentric orifice.

22. The multi-headed ink-jet system of claim 21, wherein a first liquid flows from a first reservoir through a first conduit to the outer chamber of the outer concentric piezoelectric member to be ejected through the concentric orifice, and wherein the first liquid includes an encapsulating agent.

23. The multi-headed ink-jet system of claim 16, wherein the inner chamber of the outer concentric piezoelectric member is in fluid communication with a second exit port in the concentric orifice.

24. The multi-headed ink-jet system of claim 23, wherein a second liquid flows from a second reservoir through a second conduit to the inner chamber of the inner concentric piezoelectric member to be ejected through the concentric orifice, and wherein the second liquid includes an encapsulant.

25. The multi-headed ink-jet system of claim 15, wherein the concentric orifice includes a first exit port in liquid communication with the outer chamber and a second exit port in liquid communication with the inner chamber.

26. The multi-headed ink-jet system of claim 15, wherein each of the inner and outer conductive coatings of each of the inner and outer concentric piezoeleotric members is individually actuated by a power source controlled by a controller.

27. The multi-headed ink-jet system of claim 26, wherein actuation of each of the inner and outer conductive coatings a of the inner concentric piezoelectric member results in deformation of both the inner chamber of the inner concentric piezoelectric member and the deformation of the outer chamber of the outer concentric piezoelectric member.

28. The multi-headed ink-jet system of claim 26, wherein actuation of each of the inner and outer conductive coatings of the outer concentric piezoelectric member results in deformation of only the outer chamber of the outer concentric piezoelectric member without affecting the inner chamber of the inner concentric piezoelectric member.

* * * * *